US011401543B2

(12) United States Patent
Goldrick et al.

(10) Patent No.: US 11,401,543 B2
(45) Date of Patent: Aug. 2, 2022

(54) METHODS AND COMPOSITIONS FOR IMPROVING REMOVAL OF RIBOSOMAL RNA FROM BIOLOGICAL SAMPLES

(71) Applicant: BIOO Scientific Corporation, Austin, TX (US)

(72) Inventors: Marianna Goldrick, Austin, TX (US); Lance Lepovitz, Austin, TX (US); Masoud Toloue, Austin, TX (US)

(73) Assignee: BIOO Scientific Corporation, Austin, TX (US)

( * ) Notice: Subject to any disclaimer, the term of this patent is extended or adjusted under 35 U.S.C. 154(b) by 131 days.

(21) Appl. No.: 16/440,582

(22) Filed: Jun. 13, 2019

(65) Prior Publication Data

US 2019/0330682 A1 Oct. 31, 2019

Related U.S. Application Data

(63) Continuation of application No. 14/040,117, filed on Sep. 27, 2013, now Pat. No. 10,364,455.

(60) Provisional application No. 61/736,933, filed on Dec. 13, 2012, provisional application No. 61/706,361, filed on Sep. 27, 2012.

(51) Int. Cl.
*C12Q 1/68* (2018.01)
*C12Q 1/6806* (2018.01)

(52) U.S. Cl.
CPC .................. *C12Q 1/6806* (2013.01)

(58) Field of Classification Search
USPC ......... 435/6.1, 6.11, 91.1, 183; 436/94, 501; 536/23.1, 24.3
See application file for complete search history.

(56) References Cited

U.S. PATENT DOCUMENTS

| | | | |
|---|---|---|---|
| 5,512,436 A | 4/1996 | Stone et al. | |
| 5,665,554 A | 9/1997 | Reeve et al. | |
| 5,684,143 A * | 11/1997 | Gryaznov | C07H 19/10 536/23.1 |
| 5,705,628 A | 1/1998 | Hawkins et al. | |
| 10,364,455 B2 | 7/2019 | Goldrick et al. | |
| 2003/0219728 A1 | 11/2003 | Finkel et al. | |
| 2005/0164236 A1 | 7/2005 | Su et al. | |
| 2006/0160121 A1 | 7/2006 | Mounts et al. | |
| 2006/0292559 A1 | 12/2006 | Reddy et al. | |
| 2008/0293594 A1 | 11/2008 | Archer et al. | |
| 2009/0137415 A1 | 5/2009 | Freije et al. | |
| 2010/0122361 A1 | 5/2010 | Smith et al. | |
| 2011/0040081 A1 | 2/2011 | Sooknanan et al. | |
| 2011/0319283 A1 | 12/2011 | Thompson et al. | |
| 2014/0295418 A1 | 10/2014 | Goldrick et al. | |

OTHER PUBLICATIONS

Adhya et al., "Control of transcription termination," Annu. Rev. Biochem., 1978, 47:967-996.
Amasino et al., "Acceleration of nucleic acid hybridization by polyethylene glycol," Anal. Biochem., 1986, 152:304-307.
Aziz et al., "Improving poor in vitro transcription from G,C-rich genes," Nucleic Acids Res., 1990, 18(11):3418.
Bastard et al., "RNA isolation and purification methods," Ann. Biol. Clin. (Paris), 2002, 60(5):513-523 [English abstract only].
Bryksin et al. "Overlap extension PCR cloning: a simple and reliable way to create recombinant plasmids," Biotechniques, 2010, 48(6):463-465.
Chollet et al., "Biotin-labeled synthetic oligodeoxyribonucleotides: chemical synthesis and uses as hybridization probes," Nucleic Acids Res., 1985, 13(5):1529-1541.
Chomcznski et al., "Solubilization in formamide protects RNA from degradation," Nucleic Acids Res., 1992, 20(14):3791-3792.
Delius et al., "Separation of complementary strands of plasmid DNA using the biotin-avidin system and its application to heteroduplex formation and RNA/DNA hybridizations in electron microscopy," Nucleic Acids Res., 1985, 13(15):5457-5469.
Evers et al., "Paraffin embedding contributes to RNA aggregation, reduced RNA yield, and low RNA quality," J. Mol. Diagn., 2011, 13(6):687-194.
Hubé et al., "Improved PCR method for amplification of GC-rich DNA sequences," Mol. Biotechnol., 2005, 31(1):81-84.
Jakobsen et al., "Purification of mRNA directly from crude plant tissues in 15 minutes using magnetic oligo dT microspheres," Nucleic Acid Res., 1990, 18(12):3669.
Kibriya et al., "Analyses and interpretation of whole-genome gene expression from formalin-fixed paraffin-embedded tissue: an illustration with breast cancer tissues," BMC Genomics, 2010, 11:622, 23 pages.
Lal et al., "Capture of MicroRNA-bound mRNAs identifies the tumor suppressor miR-34a as a regulator of growth factor signaling," PLoS Genet., 2011, 7(11):e1002363, 17 pages.
Lewis et al., "Unlocking the archive-gene expression in paraffin-embedded tissue," J. Pathol., 2001, 195(1):66-71.
Melton et al., "Efficient in vitro synthesis of biologically active RNA and RNA hybridization probes from plasmids containing a bacteriophage SP6 promoter," Nucleic Acids Res., 1984, 12(18):7035-7056.
Nucleotide comparison between SEQ ID No. 2 and human 28S rRNA. Printed on May 13, 2017.
Ribaudo et al., "Preparation of RNA from tissues and cells," Curr. Protoc. Immunol., 2001, (DOI: 10.1002/0471142735.im1011s04), 14 pages.

(Continued)

*Primary Examiner* — Frank W Lu
(74) *Attorney, Agent, or Firm* — Fish & Richardson P.C.

(57) ABSTRACT

The invention generally relates to compositions for maximizing capture of affinity-labeled molecules on solid supports. The disclosed methods and compositions were developed to maximize depletion of ribosomal RNA from total RNA samples, which is useful to improve the quality of RNA preparations used for applications such as massively parallel sequencing. The RNA depletion method is based on using long affinity-labeled RNA molecules that are complementary to all or part of the target ribosomal RNAs, as subtractive hybridization probes.

7 Claims, 3 Drawing Sheets

Specification includes a Sequence Listing.

(56) References Cited

OTHER PUBLICATIONS

Rong et al., "Promoter specificity determinants of T7 RNA polymerase," PNAS USA, 1998, 95:515-519.
Yi et al., "Duplex-specific nuclease efficiently removes rRNA for prokaryotic RNA-seq," Nucleic Acids Res., 2011, 39(20):1-9.

* cited by examiner

METHODS AND COMPOSITIONS FOR IMPROVING REMOVAL OF RIBOSOMAL RNA FROM BIOLOGICAL SAMPLES

CROSS-REFERENCE TO RELATED APPLICATIONS

This application is a continuation application of and claims priority to U.S. application Ser. No. 14/040,117 filed on Sep. 27, 2013, now U.S. Pat. No. 10,364,455 issued on Jul. 30, 2019; which claims the benefit of U.S. Provisional Application No. 61/706,361 filed on Sep. 27, 2012 and U.S. Provisional Application No. 61/736,933 filed on Dec. 13, 2012. Each application is hereby incorporated herein by reference.

BACKGROUND OF THE INVENTION

1. Field of the Invention

The invention generally relates to molecular biology, specifically to methods and compositions for maximizing capture of affinity-labeled RNA complexes onto magnetic beads coupled to affinity capture moieties. The invention is especially useful in the context of removing ribosomal RNA and other unwanted RNAs from RNA samples prior to analyzing the samples, and especially for RNA analysis using massively parallel sequencing.

2. DESCRIPTION OF THE RELEVANT ART

"Sequencing" is the term used to describe the process of determining the order of nucleotides in polynucleotide molecules, typically genomic DNA and RNA. The technology for sequencing has evolved over the several decades since it was first invented. Initially, sequencing required clonal amplification of individual target molecules in plasmid or phage vectors, and the resulting templates were then sequenced in individual reactions and analyzed in separate lanes of high resolution polyacrylamide gels or, after the invention of automated sequencing, in separate channels or capillaries. More recently, newer sequencing technologies have been invented, that rely on simultaneous amplification of complex populations of DNA or RNA targets using the polymerase chain reaction (PCR). The complex populations may comprise fragments of DNA derived from whole genomes of cells or tissues, or the entire populations of RNAs ("transcriptomes") present in cells or tissues. The amplified populations are then sequenced in parallel, enabling much higher throughput in acquisition of sequencing data, and at a much reduced cost. The newer methods are often referred to as "massively parallel sequencing" or "next generation sequencing" (NGS).

The amplified populations of complex DNA or RNA molecules are often referred to as "libraries", and are produced by using the primary genetic material (as may be obtained for example by extraction of DNA or RNA from malignant tumor cells or from healthy normal cells) as input for a series of enzymatic modifications catalyzed by enzymes commonly used for molecular biology applications. Examples of such enzymes are RNA and DNA polymerases, RNA and DNA ligases, reverse transcriptase, thermostable DNA polymerase, etc. The enzymatic steps serve to introduce specific synthetic oliogonucleotide sequences into the primary target material, said sequences being necessary for exponentially increasing the number of target molecules by PCR (known as "amplifying the library") to levels required for sequencing, and for adding sequences required for associating the library with the NGS instrument. The new sequencing technologies have enabled unprecedented ability to acquire genomic data, for example to determine sequences of entire genomes, and to determine the entire RNA output (known as "transcriptome profiling" or "global expression profiling") of particular cells and tissues. RNA output can refer to traditional mRNAs that reflect protein-coding sequences, or non-coding RNAs including microRNAs and other small RNAs, as well as long non-coding RNAs.

A challenge for NGS is that target molecules to be analyzed are not clonally amplified, and the complex populations that comprise the sample to be analyzed contain a preponderance of contaminating sequences that are not of interest. For example, RNA samples are highly contaminated with ribosomal RNA (rRNA), which comprises ~85% of the mass of total RNA extracted from biological samples such as human tissues and cell lines. It is desirable to remove rRNA prior to using the RNA sample for NGS, to avoid the cost in materials and data analysis associated with sequencing rRNA, and also to allow more sensitive detection of sequences of interest.

Several methods exist for removal or depletion of rRNA from total RNA samples. One method is to positively select polyadenylated RNAs using oligo-dT affinity reagents, thereby eliminating the rRNA from the recovered material. The polythymidine tracts in the oligo dT affinity reagents hybridize to the polyA regions that occur at the 3' ends of most messenger RNAs (mRNAs), allowing these mRNAs of interest to be physically removed from the total RNA population. Disadvantages of poly A selection is that in some RNAs of interest, such as bacteria mRNAs, long noncoding RNAs and some eukaryotic mRNAs, are not polyadenylated and are therefore lost during the selection. Additionally, differences in length of the polyA tract between different mRNAS may lead to inefficient capture of mRNAs with short poly A regions, resulting in bias in the population of selected mRNAs. Another major drawback of poly A selection is that when applied to fragmented RNA, only the fragments from the 3' ends of the mRNAs, containing the polyA capture regions, will be recovered. The RNA extracted from formalin fixed paraffin embedded (FFPE) tissues is recovered in highly fragmented form, and so poly A selection results in loss of sequencing information from all except the 3' regions of mRNA. Information from most regions of the target genes, for example the presence of mutations and splicing isoforms, is lost when using poly A selection to recover rRNA-depleted mRNA from FFPE samples. This is a significant shortcoming, since there is high interest in using archived FFPE tissues from pathological samples such as tumors, to carry out RNA analysis using NGS. The goal is to discover biomarkers based on differences in mRNA or non-coding RNA patterns that are associated with cancer and other pathologies.

Other methods used to eliminate rRNA include subtractive hybridization with DNA probes, where capture DNA oligonucleotides complementary to short regions (less than ~100 nucleotides) of rRNA are hybridized to the sample, followed by removal of the capture oligo/rRNA complexes. The capture oligos may be synthesized with a biotin modification at one end, to allow removal of the complexes by streptavidin affinity reagents such as streptavidin magnetic beads. Biotin-streptavidin approaches for affinity purification are widely used in various molecular and cell biology applications including purification of proteins, antibodies, and nucleic acids. Several commercial products are available for subtractive hybridization-based removal of rRNA, which use proprietary methods that are likely based on using rRNA-complementary capture oligonucleotides comprising DNA. An example of such a kit is the RiboMinus kit is sold by Life Technologies.

A related method, which is the subject of U.S. Patent Application No. 2011/0040081, uses rRNA-complementary affinity-labeled subtractive hybridization RNA probes for rRNA depletion. In a preferred embodiment, the probes are labeled with biotin and the rRNA/probe complexes are removed by capture onto a streptaviden solid support, such as magnetic beads. The technology described in the application may be that which is used in the commercially-available RiboZero kit from Epicenter.

Commercially available kits for rRNA depletion are expensive and the rRNA depletion has been reported to be unreliable, in the case of the RiboMinus kit, for thoroughly depleting rRNA (for example, see recent posts related to rRNA depletion in SEQAnswers, an on-line discussion forum and information source for next generation sequencing, at seqanswers.com). Methods based on use of short rRNA-complementary DNA oligos are expected to be inefficient for removing fragmented rRNA such as that recovered from FFPE samples, since not all of the fragments will include the sequences complementary to the capture oligonucleotides.

Another approach for depletion of rRNA uses double-strand-specific nucleases (enzymes that digest DNA and/or RNA) to digest rRNA that is hybridized to complementary DNA strands.

Examples of nucleases used for this application include RNase H, which degrades the RNA strand in RNA/DNA heteroduplexes, and DSN (double strand nuclease), which can digest RNA/DNA and DNA/DNA duplexes. Disadvantages of nuclease methods include high cost, complicated protocols that require fragmentation of the RNA and conversion to cDNA prior to nuclease treatment, and the possibility that the nucleases will digest target RNAs of interest.

SUMMARY OF THE INVENTION

A method for removing rRNA from an rRNA-containing sample includes: obtaining an RNA sample from a biological source, said RNA sample containing rRNA; mixing said RNA sample with one or more RNA subtractive hybridization probe(s) which is/are complementary to one or more rRNA molecules in the RNA sample, wherein the RNA subtractive hybridization probe(s) comprise an affinity label; incubating the RNA sample/RNA subtractive hybridization probe mixture under conditions effective to allow hybridization of the probe(s) with the rRNA in the sample RNA; incubating the hybridized probe rRNA mixture under conditions effective to associate the affinity label in the hybridized probe/rRNA complex with a solid support by linking it to an affinity label recognition molecule attached to the solid support, wherein incubating the hybridized probe rRNA mixture is carried out in the presence of a reaction composition containing components that facilitate association of the hybridized probe/rRNA with the solid support; removing the hybridized probe/sample RNA/solid support complex; and recovering the remaining RNA in the sample.

In an embodiment, the reaction composition includes polyethylene glycol and divalent cations. The reaction composition may include comprises polyethylene glycol present at a concentration of between about 2% and 25%. The reaction composition may include magnesium ions present at a concentration of between about 3 mM and 30 mM.

In a specific embodiment, one or more of the RNA subtractive hybridization probes is/are complementary to two or more regions of 28S rRNA that are discontinuously encoded in the genome, said regions chosen to eliminate inclusion of G-C-rich regions that normally lie between the discontinuous regions comprising the RNA probe.

In another embodiment, a method for removing one or more abundant RNAs from an RNA sample, includes: obtaining an RNA sample from a biological source, said RNA sample containing one or more abundant RNAs, where said abundant RNAs are defined as being present at levels that compromise detection or quantification of less abundant RNAs; mixing said RNA sample with one or more RNA subtractive hybridization probe(s) which is/are complementary to one or more rRNA molecules in the RNA sample, wherein the RNA subtractive hybridization probe(s) comprise an affinity label; incubating the mixture under conditions effective to allow hybridization of the probe(s) with the rRNA in the sample RNA; incubating the mixture under conditions effective to associate the affinity label in the hybridized probe/rRNA complex with a solid support by linking it to an affinity label recognition molecule attached to the solid support, wherein the incubation of the hybridized probe/rRNA complex is carried out in the presence of a reaction composition containing components that facilitate association of the hybridized probe/rRNA with the solid support; removing the hybridized probe/sample RNA/solid support complex; and recovering the remaining RNA in the sample.

In an embodiment, the reaction composition includes polyethylene glycol and divalent cations. The reaction composition may include comprises polyethylene glycol present at a concentration of between about 2% and 25%. The reaction composition may include magnesium ions present at a concentration of between about 3 mM and 30 mM.

The abundant RNA(s) may be coding RNAs (e.g., messenger RNAs). In another embodiment, the abundant RNA(s) codes for all or part of globin genes. The RNA sample may be obtained from prokaryotic cells. In another embodiment, the RNA sample comprises a mixture of RNA from eukaryotic and prokaryotic cells.

In an embodiment, a kit for removing rRNA from an rRNA-containing sample, includes one or more RNA subtractive hybridization probes, said probes synthesized such that they include modified bases; a solid support conjugated with a capture substance that binds to the modification on the bases used to synthesize the subtractive hybridization probes; and a reaction composition containing components effective to facilitate binding of the capture substance with the modification present in the RNA subtractive hybridization probes.

BRIEF DESCRIPTION OF THE DRAWINGS

Advantages of the present invention will become apparent to those skilled in the art with the benefit of the following detailed description of embodiments and upon reference to the accompanying drawings in which.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

It is to be understood the present invention is not limited to particular devices or methods, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected.

Described herein are improved methods and compositions to allow use of synthetic RNA subtractive hybridization probes, which are synthetic RNA molecule(s) complementary to rRNA or other RNA which is targeted for depletion, to remove unwanted RNA.

Methods and compositions for maximizing capture of affinity-labeled molecules on solid supports, for example magnetic beads, were developed to maximize depletion of ribosomal RNA from total RNA samples, which is useful to improve the quality of RNA preparations used for applications such as massively parallel sequencing. The RNA depletion method is based on using long affinity-labeled RNA molecules that are complementary to all or part of the target ribosomal RNAs, as subtractive hybridization probes. The probes may be synthesized with incorporation of nucleotide bases containing modifications such as biotin, to allow the probe/ribosomal RNA complexes to be physically removed from the RNA preparation by capture of the complexes onto suitable solid supports, such as magnetic beads conjugated to streptavidin. A novel reaction composition is used for capturing the complex onto the solid support.

Initially, we explored use of biotinylated rRNA-complementary RNA probes for rRNA depletion. Our attempts to capture the rRNA/probe complexes on streptaviden magnetic beads demonstrated that the streptaviden magnetic beads from some vendors were ineffective for removing the complexes, while those from other vendors nonspecifically removed all RNA, not only the targeted rRNA. We identified one commercial source for magnetic beads (SoluLink Inc) that showed superior ability to specifically remove the rRNA/probe complexes, to the extent that the targeted rRNA was completely removed as assessed by agarose gel electrophoresis of the reaction products. However, a more sensitive RT-qPCR assay showed that some of the rRNA/probe complexes, and/or some of the free probe molecules, were not completely captured by the SoluLink streptavidin magnetic beads, when the capture step was carried out using the buffer composition recommended by SoluLink. We therefore carried out studies to identify a better capture buffer. As a result, we identified a novel buffer that improved capture of biotinylated RNA probes. In the course of designing the rRNA-complementary probes, we also developed novel methods for designing the DNA templates used to generate the probes. The novel template designs result in higher yields of probes, and probes with improved properties, for example better ability to deplete rRNA. The improved performance of the probes is likely due to the fact that the novel design avoids highly GC rich regions that occur in natural rRNA sequences and produces probes having less stable secondary structures. Taken together, our methods enable production of deliberately engineered long RNAs as subtractive hybridization probes, which, when used in conjunction with our novel reagent specially formulated to facilitate capture of the rRNA/RNA probe complexes onto streptavidin magnetic beads, result in more complete removal of rRNA from total RNA samples.

The probes used in the methods described herein are typically at least several hundred bases in length, which distinguishes them from short DNA oligos used previously as subtractive rRNA probes. An advantage of the RNA probes described herein is that their longer size allows more rapid and thorough hybridization to rRNA. Additionally, the fact that RNA/RNA duplexes are more stable than RNA/DNA duplexes allows the hybridization to be carried out under more stringent conditions (higher temperature, lower ionic strength), which can result in more specific hybridization of the probes to their rRNA targets, with less non-specific hybridization to mRNAs or other RNAs of interest. Also, the fact that the RNA probes are single-stranded allows them to hybridize with the target rRNA without interference from a complementary probe strand, as would be the case if longer double-strand DNA probes were used. Other advantages inherent in the use of the RNA probes described herein are that the RNA probes can be synthesized at comparatively low cost, and they can be produced to include specific modifications useful for their subsequent removal after hybridization to their rRNA (or other undesirable RNA) targets. In an embodiment, the method includes a process for the capture and physical removal of the probe/rRNA complexes subsequent to the probe/rRNA hybridization step.

Subtractive RNA hybridization probes are typically synthesized by a phage RNA polymerase such as T7 RNA Polymerase by the process known as in vitro transcription (IVT), with incorporation of a modified ribonucleotide triphosphate (NTP) during the IVT, said modified NTP serving as a capture sequence for the affinity-based removal of the complex. Examples of suitable modified NTPs include biotin-UTP or biotin-CTP. Incorporation of biotinylated NTPs into the subtractive probes allow the rRNA/probe complexes to be physically removed by capture onto suitable streptavidin-conjugated solid supports, for example streptavidin-conjugated magnetic beads. The rRNA-depleted sample can then be recovered and used as input for NGS or other applications.

In one embodiment, a method of increasing the capture of affinity-modified subtractive RNA hybridization probes onto solid supports comprising the corresponding affinity-recognition molecules is described. In an embodiment, the affinity modification in the subtractive RNA hybridization probe is biotin, and the affinity-recognition molecule on the solid support is streptaviden or related molecule (for example aviden-related molecules or compounds). To accomplish the goal of depleting an undesired RNA from an RNA sample, the subtractive RNA hybridization probe, which comprises regions complementary to the undesired RNA, is mixed with sample RNA and stored under conditions that allow hybridization of the probe with the undesired RNA (e.g. rRNA) in the sample. After hybridization of the affinity-labeled probe to the sample RNA, the probe/undesired RNA complex is associated with a solid support. In an embodiment, the solid support is attached to streptavidin or a similar structure (e.g. neutravidin), which allows association of the probe/rRNA complex through binding of biotin modifications in the probe to the solid support.

The disclosed method, in some embodiments, uses a reaction solution composition that assists with the association of the probe/rRNA complex with the solid support. Specifically, the reaction solution composition includes polyethylene glycol and magnesium ions. The tripartite complex comprising probe/rRNA/solid support may then be physically removed from the reaction mixture, leaving the rRNA-depleted RNA sample behind. The RNA remaining in the depleted sample may then be used for downstream applications such as input for NGS library construction. The steps of the method are described in detail in the following sections. Another aspect of the disclosed methods relate to the sequence of the DNA template used to produce the subtractive RNA hybridization probe. Specifically, a method relates to design and use of a synthetic DNA template comprising regions of complementarity to discontinuous regions of the undesired RNA, for example rRNA.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.
1. Preparation of Template for Synthesis of the Probe Via IVT.

In one embodiment, a subtractive RNA hybridization probe is synthesized using a phage polymerase, for example T7 RNA polymerase, to transcribe a suitable DNA template into RNA. The DNA template includes the DNA sequence corresponding to all or part of one or more rRNAs, and a T7 promoter consensus sequence positioned in the template in such a way that the transcribed RNA is complementary to one or more ribosomal RNAs. The T7 consensus sequence is 5'-TAATACGACTCACTATAGGG (SEQ ID NO. 1). The DNA template for IVT includes a plasmid vector containing the rRNA sequence and the promoter. In an embodiment, the DNA template can be produced using PCR. To make the template using PCR, suitable primers are designed to amplify a region of rRNA where the Reverse PCR primer comprises a T7 promoter on the 5' side of the sequence complementary to the rRNA target. The PCR product can be used directly as template, or it can be purified to remove unincorporated PCR primers and dNTPs prior to use.

In an embodiment, a fused PCR template is designed, which contains a T7 promoter and amplicons comprising two or more segments of rRNA sequence, where said segments are non-contiguous in the genomic sequence encoding the rRNAs. For example, a PCR template was constructed by fusing the amplicons for human 5S rRNA, 5.8S rRNA, and a 788 bp region of human 18S rRNA. The resulting fused PCR template is used to synthesize a subtractive rRNA probe capable of removing all 3 rRNA species (5S, 5.8S, and 18S). Using a fused PCR template simplifies the production of subtractive hybridization probes and enables simultaneous removal of multiple species of rRNA. Fusion of amplicons derived from non-contiguous chromosomal regions can be accomplished using various methods familiar to those skilled in the art, for example using gene synthesis or overlap extension methodologies.

Fused PCR templates are also useful for constructing templates that avoid problematic sequences present in rRNA. For example, human 28S rRNA contains regions of exceptionally high GC content, including regions comprising homopolymeric sequences of 5-11 G's or C's. Such regions represent obstacles to efficient polymerization by DNA polymerases such as Taq polymerase used in PCR, and also present obstacles to transcription of the template by T7 RNA polymerase. Fusion templates that avoid these problematic regions, but that still include regions of 28S rRNA sequence present at the 5' and 3' sides as well as in centrally located regions of the 28S rRNA sequence, can be constructed by fusing amplicons derived from discontinuous regions of 28S rRNA, said discontinuous regions chosen to avoid the problematic GC-rich regions. Use of probes transcribed from such discontinuous templates may allow efficient subtraction of fragmented 28S rRNA, such as are recovered from FFPE tissues. A possible disadvantage of using probes that avoid GC-rich regions is that they would not remove fragmented rRNA comprising the GC-rich regions. However, such GC-rich regions may be underrepresented in NGS libraries, since the GC-rich regions are likely to present obstacles to the enzymes used for the ligation, reverse transcription, and amplification steps used to produce the NGS libraries. To address this issue, we analyzed the NGS coverage of the human 28S rRNA gene located on Chromosome 1 (the human genome contains multiple genes for rRNA which are dispersed on different chromosomes but which are all highly similar, differing by less than ~1%). We noted that the coverage is low in the exceptionally GC-rich regions. Thus, human 28S rRNA presents a target that can be used to test PCR templates that specifically avoid these problematic GC-rich regions. The low sequence coverage of rRNA-derived GC-rich regions in NGS sequencing reads, which was revealed by our analysis of publically available NGS data, means that there is not a high requirement for depleting rRNA fragments comprising these problematic regions of 28S rRNA from total RNA samples prior to constructing NGS libraries.

The PCR templates used in the IVT to make the RNA probes for depletion of rRNA can be produced by amplification of contiguous regions of several hundred bases of 28S, 18S, 5.8S, and/or 5S rRNA sequences from genomic DNA isolated from whole blood or other sources. Amplification can be carried out using PCR with suitably designed primers. The templates for rRNA hybridization probes can also be made using alternative strategies, where the templates are not generated from genomic DNA extracted from biological sources. For example, templates for IVT can be created by de novo synthesis of blocks of several hundred nucleotides, comprising appropriately chosen regions of 28S rRNA which are discontinuous in the genome. The synthetic templates may then be amplified by PCR to create large mass amounts of the templates for long-term use, at a nominal cost. The synthetic templates can be designed to include phage promoter sequences, for example T7 promoter sequences, or the promoter sequences can be added during the PCR amplification step, by incorporating the sequences into the Forward or Reverse PCR primers. It will be appreciated by those skilled in the art, that the decision on whether to incorporate a phage promoter sequence into the Forward or the Reverse PCR primer depends on the orientation of the rRNA sequences (or orientation of other sequences to be depleted from the input RNA sample) within the synthetic template. The promoter sequences must be added to the Forward or Reverse primer as appropriate to generate the complement of the rRNA sequence (or other sequence to be depleted) in the in vitro transcription product.

2. Synthesis of RNA Subtractive Hybridization Probe by In Vitro Transcription (IVT)

The templates are used to generate rRNA-complementary transcripts using methods known to those skilled in the art. The following describes the detailed protocol used to for the IVT step to make an rRNA subtractive hybridization probe for 18S rRNA. Similar protocols were used to make probes for subtraction of 28S rRNA, and for subtraction of 18S+ 5.8S+5S rRNA, using a fused PCR product as described above.

The IVT used the T7 High Yield RNA Synthesis Kit (cat #E2040S) purchased from New England Biolabs (240 County Road, Ipswich Mass. 01938-2723; www.neb.com). The protocol was modified to include biotinylated UTP (cat #BU6105H: 50 mM biotin-16-UTP), which was purchased from Epicentre Biotechnology (726 Post Road Madison Wis. 53713, 800-284-8474). Biotin-UTP was included at a final concentration of 1.25 mM and unmodified UTP was included at concentration of 3.75 mM. Another modification in the protocol was that the final concentration of all NTPs was reduced to 5 mM (instead of 10 mM used in the NEB standard protocol). The IVT reaction was carried out as follows:

The following components were mixed in a 1.5 ml microfuge tube:
- 2 uL of purified PCR template (137 ng/uL), containing a T7 promoter and 788 bp of human 18S rRNA sequence
- 2 uL 10× reaction buffer
- 1 uL 100 mM ATP
- 1 uL 100 mM GTP
- 1 uL 100 mM CTP
- 0.75 uL 100 mM UTP
- 0.5 uL 50 mM biotin-UTP
- 2 uL T7 enzyme mix
- 9.75 uL water The reaction was incubated for 2 hours at 37° C., then 90 µL of water was added. The RNA transcript was purified using carboxylated magnetic beads using standard methods known to those skilled in the art. The concentration of the purified transcript was determined by spectrophotometric analysis in a nanodrop instrument and found to be 805 ng/µL. The purity and size of the transcript were analyzed on a 1.2% agarose gel. Gel analysis confirmed the expected size of the transcript and thorough removal of PCR primer-dimer side-products.

3. Extraction of Total RNA. Total RNA Containing rRNA was Extracted from a Biological Source, Cultured Human T Cells (Cell Line 293)

Cells were collected by low-speed centrifugation and RNA was extracted from the pelleted cells using BiooPure RNA Extraction Reagent (Bioo Scientific) according to the manufacture's protocol. The RNA was resuspended in 0.1 mM EDTA, and assessed by nanodrop and agarose gel electrophoresis. The RNA was adjusted to convenient working concentrations, typically 1 mg/mL.

4. Hybridization of Total RNA with Subtractive Hybridization Probe

The following describes a typical example of using the disclosed method to deplete 18S and 28S rRNA from 2 µg of total RNA. The following components were mixed in a 1.5 mL microfuge tube:
- 2 µg total RNA (in volume of 2 µL)
- 350 ng of RNA subtractive hybridization probe for 18S rRNA
- 600 ng of RNA subtractive hybridization probe for 28S rRNA
- 5.2 µL of buffer (80% formamide/100 mM NaCl/10 mM Tris 7/3 mM EDTA)

The 10 µL reaction was incubated for 10 min. at room temp, then for 10 min. at 55° C. An aliquot of the reaction was analyzed on a 1.2% native agarose gel, along with an equivalent mass amount of total RNA which had not been hybridized to the probe (used as control).

Figure 1:
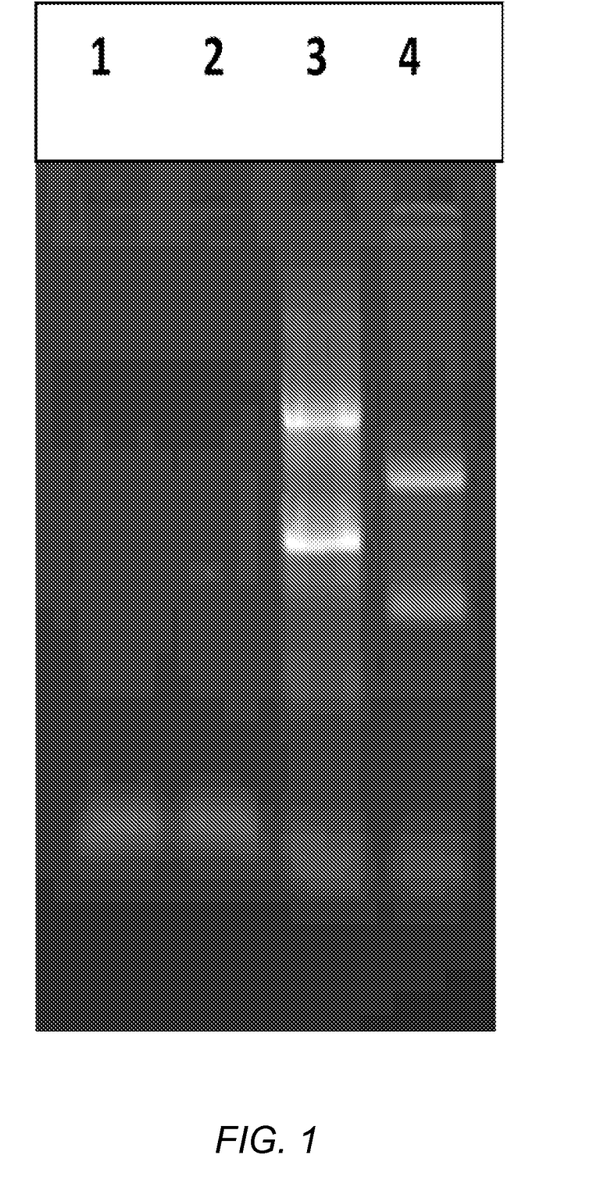
FIG. 1 depicts complete removal of hybridized biotinylated probe/rRNA complexes by capture onto streptavidin magnetic beads.

FIG. 1 shows the complete removal of hybridized biotinylated probe/rRNA complexes by capture onto streptavidin magnetic beads. Lanes 1 and 2 show rRNA-depleted RNA remaining in the supernatant fluid after incubation of the hybridized sample with 10 µL (Lane 1) or 15 µL (Lane 2) of streptavidin magnetic beads (Nanolink beads from SoluLink Inc). Samples were incubated for 30 min. with agitation on a vortex mixer, in 30 µL of reaction buffer comprising 150 mM NaCl/5% PEG 8000/10 mM $MgCl_2$, to capture of the hybridized probe/rRNA complexes (shown in Lane 3) onto the streptavidin beads. Samples were then placed on a magnetic stand (SoluLink cat #S-6001) for approx. 10 seconds to attract the beads along with the captured rRNA/ RNA, and the supernatant fluid was removed and analyzed by agarose gel as shown in FIG. 1. Lanes 3 and 4 depict hybridized RNA and unhybridized control RNA. Note the absence of the shifted bands in the samples in Lanes 1 and 2 after capture of the complex. As shown in FIG. 1, this analysis demonstrated complete hybridization of the target RNAs to the probes, as seen by the complete shift in mobility of the 18S and 28S rRNA bands in the hybridized sample, compared to their mobility in the control RNA sample.

5. Removal of the Hybridized RNA/Probe Complex

10 µL of streptavidin-conjugated magnetic beads (Nanolink Streptavidin Magnetic Beads, cat # M-1002-020) purchased from Solulink Inc (9853 Pacific Heights Blvd Suite H, San Diego Calif. 92121; 858-625-0670) were used to remove the probe/rRNA complex from 2 µg RNA hybridized to the 18S and 28S biotinylated RNA probes as described above. Prior to use, the 10 µL of beads were washed by attracting them to a magnet, removing the supernatant fluid, and resuspending them in 100 µL of 150 mM NaCl/5 mM Tris pH 7.5/2 mM EDTA. The beads were again attracted to the magnet and wash solution removed, than the beads were resuspended in 30 µL of a solution comprising 5% PEG-8000 (polyethylene glycol, avg. molecular weight 8000)/150 mM NaCl/10 mM $MgCl_2$. The rRNA/probe complex was then added (in a volume of 10 µL) and the mixture was incubated for 30 min. with constant agitation on a vortex mixer. The beads were then attracted to the magnet, and the supernatant fluid removed and analyzed on a 1.2% agarose gel. Control reactions analyzed on the same gel included hybridized RNA/probe complexes not depleted on the magnetic beads, and total RNA not hybridized to the probes.

Figure 2:
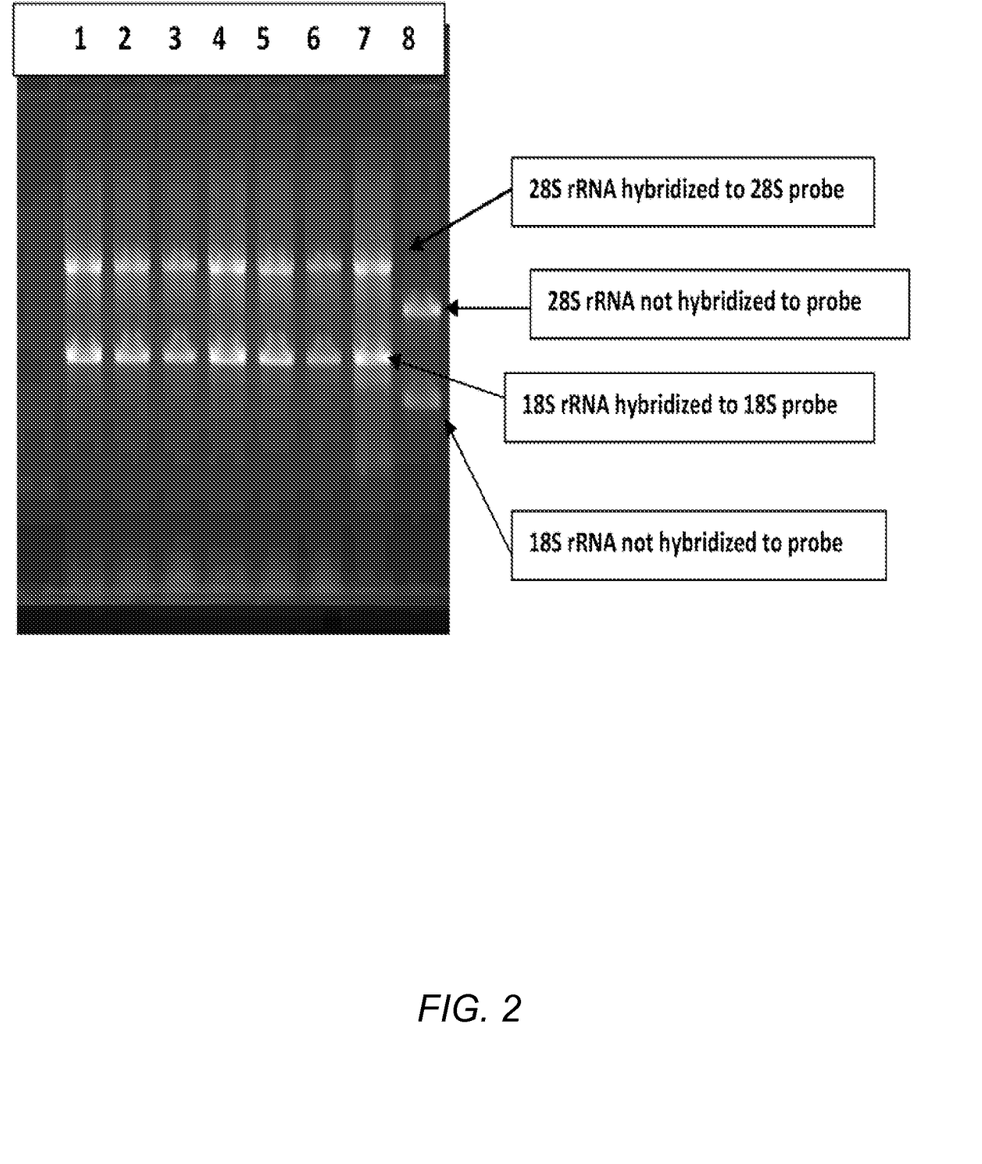
FIG. 2 depicts incomplete capture of hybridized probe/rRNA complex onto Streptavidin magnetic beads using the reaction buffer recommended by the bead manufacturer.

FIG. 2 shows the capture of hybridized probe/rRNA complex onto Streptavidin magnetic beads using the reaction buffer recommended by the bead manufacturer. Lanes 1-6 show RNA remaining in the supernatant from 293 T cells hybridized to biotinylated RNA probes for 28S and 18S RNA, and then mixed with streptavidin magnetic beads in 30 µL of reaction buffer recommended by the bead manufacturer (SoluLink Inc) and incubated under various conditions prior to attraction to the magnet and removal of supernatant as described in FIG. 2. Lane 7 shows a control sample comprised of the same amount of hybridized rRNA/probe complex which was NOT subjected to bead capture, and Lane 8 is a control RNA sample not hybridized to the probes. The composition of the reaction buffer recommended by SoluLink ("Nucleic Acid Binding and Wash Buffer") is 50 mM Tris-HCl pH 8/150 mM NaCl/0.05% Tween 20. The conditions used for bead capture were as follows: Lanes 1-3, bead capture reaction incubated for 30 min, Lanes 4-6, bead capture reactions incubated for one hour; Lanes 1 and 4: RNA complex mixed with 5 µL beads; Lanes 2 and 5: RNA complex mixed with 7.5 µL beads; Lanes 3 and 6: RNA complex mixed with 10 µL beads. Note that most of the RNA complexes were not removed by the beads using the SoluLink buffer under any conditions tested. As shown in FIG. 2, the disclosed conditions were effective to physically remove the hybridized probe/rRNA complexes from the mixture.

Figure 3:
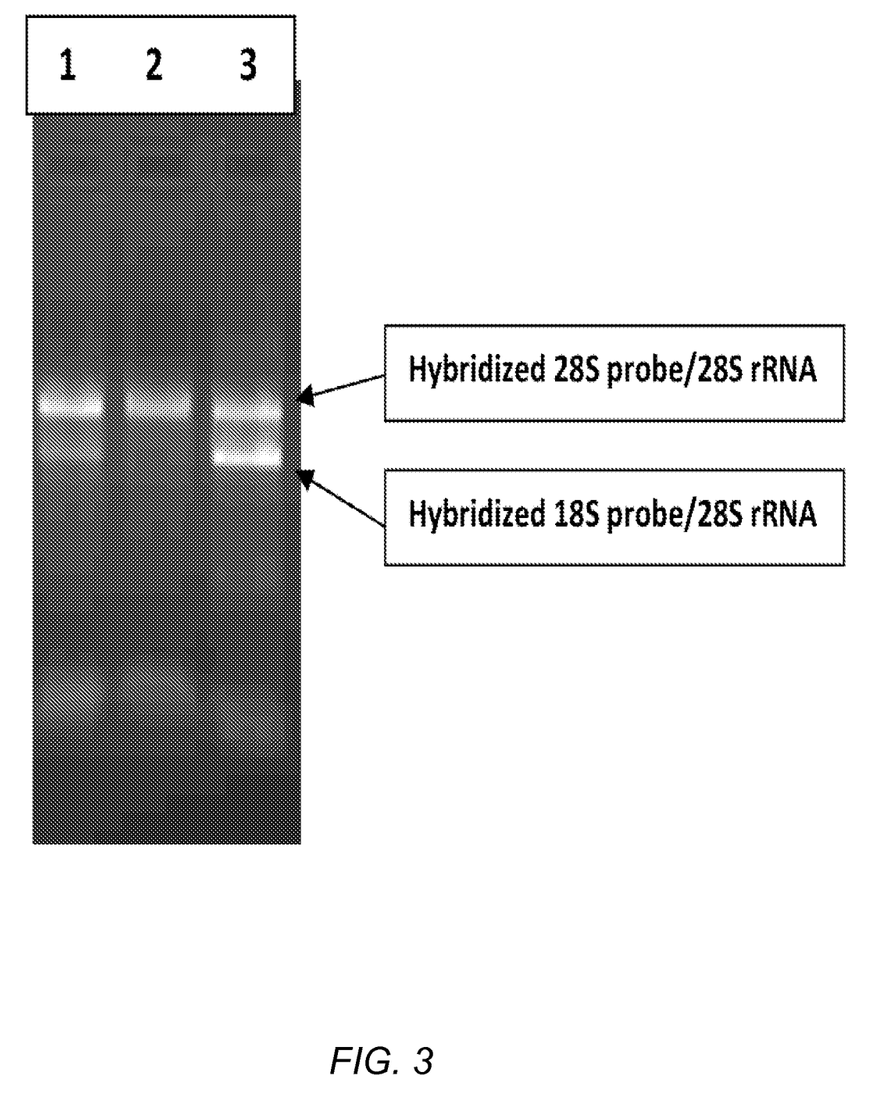
FIG. 3 depicts optimal capture of probe/rRNA complex requires both PEG and MgCl$_2$.

The particular benefit achieved by using the disclosed composition for the bead capture step is illustrated in FIG. 3. FIG. 3 depicts capture of probe/rRNA complex in the presence of both PEG and $MgCl_2$. Total RNA from 293 cells was hybridized to biotinylated probe for 18S rRNA and then mixed with streptavidin magnetic beads in 30 µL of reaction buffer comprising 150 mM NaCl/5% PEG (Lane 1) or 150 mM NaCl/5% PEG/17 mM $MgCl_2$ (Lane 2); Lane 3 is a hybridized control sample not mixed with beads. Samples were incubated for 30 min. at room temp with agitation on a vortex mixer, and then placed on a magnetic stand to attract the beads, and the supernatant fluid was removed and analyzed on an agarose gel as described in FIG. 2. The 28S rRNA band (top band) was not removed in any samples, since the RNA was not mixed with a probe for 28S rRNA. The lower band, representing the 18S probe/18S rRNA complex (as shown in FIGS. 1 and 2), was only partially removed during the bead capture step (Lane 1) when incubated in buffer containing 5% PEG but no $MgCl_2$, whereas the complex was completely removed when the buffer included both PEG and $MgCl_2$ (Lane 2).

As shown, capture of the biotinylated probe/rRNA complex onto the magnetic beads is incomplete when carried out using the reaction composition recommended by the commercial supplier of the beads (Solulink), whereas complete capture of the probe/rRNA complex is observed (FIG. 2) when the reaction composition includes polyethylene glycol (PEG) and magnesium chloride ($MgCl_2$). The $MgCl_2$ dissociates in solution to generate magnesium ions ($Mg^{++}$).

As shown in FIG. 3, capture of the complex is also incomplete when carried out in a reaction composition which includes only PEG but not $MgCl_2$. Our discovery of the synergistic effects of including two components (PEG and magnesium ions) which have not previously been used to facilitate capture of biotinylated RNA/rRNA complexes onto streptavidin magnetic beads, enables the practical application of the disclosed method. It is contemplated that other chemicals will be useful as reaction mixture components, for example other synthetic and natural polymers such as bovine serum albumin (BSA), Ficoll, and dextran sulfate; and other divalent cations such as $Mn^{++}$, $Ca^{++}$, $Zn^{++}$ or ionic variants ($NH_3^{+++}$, $SO_4^{--}$). All are contemplated as being within the scope of the disclosed method.

The use of PEG in the disclosed method differs fundamentally from that described in the prior art, in that PEG in the disclosed method is not used to accelerate hybridization of nucleic acids, but rather to facilitate association between streptavidin molecules bound to a solid support, and biotin molecules which are incorporated into the nucleic acid molecules.

6. Recovery and Use of the rRNA Depleted RNA Samples

The RNA treated according to the methods herein disclosed can be recovered by any of several methods. The most basic methods include alcohol precipitation, solid phase extraction onto silica filters, and SPRI-type purification on carboxylated magnetic beads. Any of these methods, as well as others, are contemplated to be useful for the final recovery of rRNA-depleted samples, said samples having been treated according to the methods herein described.

Equivalencies and Related Methodologies Contemplated for Use of Long Synthetic RNA probes for Depletion of rRNA It will be appreciated by those skilled in the art that many variations are possible for carrying out the various steps of the disclosed method.

1. Alternative Methods for Recovering RNA Probe/rRNA Complexes

One alternative to incorporation of biotinylated nucleotides and subsequent capture onto streptavidin-conjugated beads is to incorporate nucleotides with affinity groups or modifications other than biotin during the IVT step, for example UTP modified with bromine. The modified RNA would then be captured onto supports having suitable affinity groups, for example antibodies capable of binding to the alternative modifications.

2. Alternative Methods for Eliminating Probe/rRNA Complexes

It is also contemplated that certain aspects and embodiments of the disclosed method will be useful for removing rRNA using nuclease-based methods. For example, the methods described herein for synthesis and use of long rRNA-complementary RNA probes have obvious utility for creating the double-strand RNA molecules that could be targeted by double-strand-specific nucleases. Use of nucleases or other processes to cleave, degrade, and/or physically remove rRNA/probe complexes produced using the disclosed methods are contemplated to be within the scope of this invention.

3. Alternative Methods for Carrying Out the Sequential Steps of the Disclosed Method It will be apparent to those skilled in the art that certain of the sequential steps detailed in the disclosed methods may be carried out in a different order, without departing from the spirit and scope of the instant invention. For example, the RNA probe may be associated with the solid support prior to mixing it with the sample RNA containing rRNA. Such modifications in sequential execution of the steps of the disclosed method are contemplated to be within the scope of the disclosed methods.

4. Use of RNA Subtractive Hybridization Probes to Deplete Non-Ribosomal RNAs

In addition to depletion of ribosomal RNA, it can be beneficial to deplete other types of RNA molecules from RNA samples prior to using them as input for applications including creating libraries for RNA sequencing ("RNA-Seq") experiments. Such other types of RNA molecules include mitochondrial RNAs and mRNAs (messenger RNAs, also known as coding RNAs), especially abundant mRNAs. Examples of abundant mRNAs include Bactin, glyceraldehydes phosphate dehydrogenase, cyclophilin, and other structural RNAs and so-called "housekeeping" mRNAs, which may be constitutively present in all or most cells. Other examples of abundant RNAs which may be desirable to eliminate from RNA samples prior to sequencing, are the alpha and beta globin mRNAs found in RNA extracted from blood. Another example of abundant RNAs which may be desirable to eliminate from RNA samples prior to sequencing are common bacterial RNAs such as RNAs derived from non-pathogenic bacteria that may be present in an RNA sample comprising mixtures of pathogenic and non-pathogenic bacteria, or comprising mixtures of eukaryotic RNA and RNA from pathogenic and non-pathogenic bacteria. Other examples include RNAs from intracellular organelles such as chloroplasts. The benefit of depleting abundant RNAs from RNA samples prior to using them for next generation sequencing (NGS) is to avoid wasting sequencing and bioinformatic resources to process and analyze non-informative RNAs, and as a corollary, to allow less abundant and more interesting RNAs to be more easily detected and analyzed. An associated benefit of depleting abundant RNAs is to allow more highly multiplexed sequencing of mixed samples. Eliminating non-informative RNAs such as mitochondrial RNA and constitutively expressed mRNAs allows greater depth of coverage for sequencing RNAs of interest. Increasing coverage depth enables detection of very rare RNAs that might be missed otherwise, and/or enables simultaneous analysis of an increased number of mixed indexed RNA samples ("multiplexed samples") without sacrificing the ability to detect less abundant RNAs in the mixed samples. Using highly multiplexed NGS reduces the per sample cost of RNA-Seq experiments. It will be apparent to those skilled in the art, that use of the invention and methodologies reported herein for depleting ribosomal RNA, can also allow depletion of abundant mRNAs, mitochondrial RNAs, chloroplast RNAs, viral RNAs, bacterial RNAs, and other RNA molecules whose detection is not the focus of massively parallel sequencing experiments. For example, use of the methodologies herein reported to deplete mRNA encoding ßactin, an exceptionally abundant mRNA, would require producing a subtractive hybridization probe comprising a synthetic RNA having complementarity to all or part of ßactin mRNA, hybridizing said subtractive hybridization probe to the RNA sample, and removing the hybridized probe/ßactin mRNA complex, according to the methods described herein. The design of subtractive hybridization probes must take into account the presence of common RNA sequences that occur in the RNA to be removed as well as in RNAs that are not targeted for removal; the probes will generally be designed to exclude such common regions, and to alternatively include regions that are specific for the RNA targeted for removal. For example, to specifically remove bacterial ribosomal RNA derived from non-pathogenic *E. coli* from a sample suspected of containing potentially informative ribosomal RNA from other bacterial species, the subtractive hybridization probe can be designed to comprise the complement of all or part of the hypervariable v4 region of *E. coli* 16S ribosomal RNA. The subtractive hybridization probes may comprise sequences that are not contiguous in the RNA targeted for depletion; such non-contiguous sequences may be designed to avoid regions that are not specific to the targeted RNA, for example regions having sequence complementarity to non-targeted RNAs.

Sequences Used to Create Templates for Removal of 28S Ribosomal RNA

Disclosed below are sequences of DNA templates used to create subtractive hybridization probes for human and mouse 28S ribosomal RNA. It is anticipated that the probes will also allow removal of ribosomal RNA from other mammalian species. The sequences were synthesized by a commercial oligonucleotide synthesis company, International DNA Technologies (IDT), as Gene Blocks of approximately 500 basepairs. The sequences are referred to as Block #1-Block #6. Blocks #1-#6 span the entire region of human 28S rRNA, in the 5'-3' direction, and were designed such that they do not include problematic GC-rich regions that occur in the natural 28S rRNA sequence, and to include short regions that are not contained in the natural 28S rRNA sequence, for example TTTT "spacer" tetranucleotides positioned between regions adjacent to eliminated GC-rich regions. The Gene Blocks were amplified by PCR using Forward and Reverse primers with binding sites at the 5' and 3' ends of each block, respectively. The Reverse primers were designed to contain the T7 promoter consensus sequence at their 5' ends. The resulting PCR products ("amplicons") obtained using the Forward and T7-Reverse primers may be purified to remove unincorporated primers and dNTPs, as well as short non-specific products, and then used as templates for producing the subtractive hybridization probes by in vitro transcription with T7 RNA polymerase.

Block #1:

(SEQ ID NO. 2)

5'CGCGACCTCAGATCAGACGTGGCGACCCGCTGAATTTAAGCATATTAG

TCAGCGGAGGAGAAGAAACTAACCAGGATTCCCTCAGTAACGGCGAGTGA

ACAGGGAAGAGCCCAGCGCCGAATCCTTTTGGACATGTGGCGTACGGAAG

ACCCGCTCCTTTTCCAAGTCCTTCTGATCGAGGCCCAGCCCGTGGACGGT

GTGAGGCCGGTAGCTTTTGGTCTTCCCGGAGTCGGGTTGCTTGGGAATGC

AGCCCAAAGCGGGTGGTAAACTCCATCTAAGGCTAAATACCGGCACGAGA

CCGATAGTCAACAAGTACCGTAAGGGAAAGTTGAAAAGAACTTTGAAGAG

AGAGTTCAAGAGGGCGTGAAACCGTTAAGAGGTAAACGGGTGGTTTTCCT

CCCGACCCCTCCACCCTTTTACCGGCTCCGGGACGGCTGGGAAGGTTTTC

GACGTCGGCTACCCACCCGACCCGTCTTGAAACACGGACCAAGGAGT

CT-3'

Block #2:

(SEQ ID NO. 3)

5'AACACGTGCGCGAGTCGGTTTTGGCTCGCACGAAAGCCGCCGTGGCGC

AATGAAGGTGAAGGTTTTCGAGGTGGGATCCCGAGGCCTCTCCAGTCCTT

TTGGAGGTGGAGCACGAGCGCACGTGTTAGGACCCGAAAGATGGTGAACT

ATGCCTGGGCAGGGCGAAGCCAGAGGAAACTCTGGTGGAGGTCCGTAGCG

GTCCTGACGTGCAAATCGGTCGTCCGACCTGGGTATAGTTTTCGAAAGAC

TAATCGAACCATCTAGTAGCTGGTTCCCTCCGAAGTTTCCCTCAGGATAG

CTGGCGCTCTCGCAGACCCGACGCACCTTTTCCACGCAGTTTTATCCGGT

AAAGCGAATGATTAGAGGTCTTGGTTTTCGAAACGATCTCAACCTATTCT

CAAACTTTAAATGGGTAAGAAGCCCGGCTCGCTGGCGTGGAGCTTTTCGT

GGAATGCGAGTGCCTAGTGGGCCACTTTTGGTAAGCAGAACTGGCGCTG

CG-3'

Block #3:

(SEQ ID NO. 4)

5'GGATGAACCGAACGCCGGGTTAAGGCGCCCGATGCCGACGCTCATCAG

ACCTTTTCCAGAAAAGGTGTTGGTTGATATAGACAGCAGGACGGTGGCCA

TGGAAGTCGGAATCCGCTAAGGAGTGTGTAACAACTCACCTGCCGAATCA

-continued

ACTAGCCCTGAAAATGGATGGCGCTGGAGCGTCGGGCCCATACCCGGCCG

TCGCCGGCAGTCGAGAGTGGACGGGAGCTTTTCGCTGCGGTGAGCCTTGA

AGCCTAGGGTTTTGCAGGTGCAGATCTTGGTGGTAGTAGCAAATATTCAA

ACGAGAACTTTGAAGGCCGAAGTGGAGAAGGGTTCCATGTGAACAGCAGT

TGAACATGGGTCAGTCGGTCCTGAGAGATGGGCGAGCGCCGTTCCGAAGG

GACGGGCGATGGCCTCCGTTGCCCTCGGCCGATCGAAAGGGAGTCGGGTT

CAGATCCCCGAATCCGGAGTGGCGGAGATGGTTTTCGAGGCGTCC-3'

Block #4:
(SEQ ID NO. 5)
5'AGTGCGGTAACGCGACCGATCCTTTTGGAGAGTTCTCTTTTCTTTGTG

AAGGGCAGGTTTTCGTGCCTTGGAAAGCGTCGCGGTTCCGGCGGCGTCCG

GTGAGCTCTCGCTGGCCCTTGAAAATCCGTTTTGGAGAGGGTGTAAATCT

CGTTTTCGTACCCATATCCGCAGCAGGTCTCCAAGGTGAACAGCCTCTGG

CATGTTGGAACAATGTAGGTAAGGGAAGTCGGCAAGCCGGATCCGTAACT

TCGGGATAAGGATTGGCTCTAAGGGCTGGGTCGGTCGTTTTCCTAGCAGC

CGACTTAGAACTGGTGCGGACCAGGGGAATCCGACTGTTTAATTAAAACA

AAGCATCGCGAAGGTTTGGTGTTGACGCGATGTGATTTCTGCCCAGTGCT

CTGAATGTCAAAGTGAAGAAATTCAATGAAGCGCGGGTAAACGGCGGGAG

TAACTATGACTCTCTTAAGGTAGCCAAATGCCTCGTCATCTAATTAGT

GA-3'

Block #5
(SEQ ID NO. 6)
5'CGCGCATGAATGGATGAACGAGATTCCCACTGTCCCTACCTACTATCC

AGCGAAACCACAGCCAAGGGAACGGGCTTGGCGGAATCAGCTTTTGGAAA

GAAGACCCTGTTGAGCTTGACTCTAGTCTGGCACGGTGAAGAGACATGAG

AGGTGTAGAATAAGTGGGAGTTTTGGTGAAATACCACTACTCTGATCGTT

TTTTCACTGACCTTTTGGTACACCTGTCAAACGGTAACGCAGGTGTCCTA

AGGCGAGCTCAGGGAGGACAGAAACCTCCCGTGGAGCAGAAGGGCAAAAG

CTCGCTTGATCTTGATTTTCAGTACGAATACAGACCGTGAAAGCTTTTCC

TCACGATCCTTCTGACCTTTTGGGTTTTAAGCAGGAGGTGTCAGAAAAGT

TACCACAGGGATAACTGGCTTGTGGCGGCCAAGCGTTCATAGCGACGTCG

CTTTTTGATCCTTCGATGTCGGCTCTTCCTATCATTGTGAAGCAGAAT

TC-3'

Block #6:
(SEQ ID NO. 7)
5'ACCAAGCGTTGGATTGTTCACCCACTAATAGGGAACGTGAGCTGGGTT

TAGACCGTCGTGAGACAGGTTAGTTTTACCCTACTGATGATGTGTTGTTG

CCATGGTAATCCTGCTCAGTACGAGAGGAACCGCAGGTTCAGACATTTGG

TGTATGTGCTTGGCTGAGGAGCCAATGGTTTTCGAAGCTACCATCTGTGG

GATTATGACTGAACGCCTCTAAGTCAGAATCCCGCCCAGGCGGAACGATA

CGGCAGCGCCGCGGAGCCTCGGTTGGCCTCGGATAGCTTTTGGTCCGGTG

CGGAGTGCCCTTCGTCCTGGGAAACGTTTTCGTCACGCACCGCACGTTCG

TGGTTTTGAACCTGGCGCTAAACCATTCGTAGACGACCTGCTTCTGGGTC

GTTTTGGTTTCGTACGTAGCAGAGCAGCTCCCTCGCTGCGATCTATTGAA

AGTCAGCCCTCGACACAAGGGTTTGTC-3'

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for removing 18S rRNA from an RNA sample comprising:
    obtaining an RNA sample from a biological source, said RNA sample containing 18S rRNA;
    mixing said RNA sample with one or more RNA subtractive hybridization probes, thereby forming a mixture comprising the RNA sample and the one or more RNA subtractive hybridization probes, wherein the one or more RNA subtractive hybridization probes comprise an affinity label comprising biotin, and wherein the one or more of the RNA subtractive hybridization probes hybridize to two or more discontinuous regions of 18S rRNA in the RNA sample;
    incubating the mixture under conditions effective to allow hybridization of the one or more RNA subtractive hybridization probes with the 18S rRNA in the RNA sample, thereby forming a hybridized complex comprising the one or more RNA subtractive hybridization probes and the 18S rRNA;
    facilitating association of the hybridized complex with a solid support by incubating the hybridized complex with the solid support in a reaction composition, thereby forming a complex comprising the hybridized complex and the solid support, wherein the affinity label on the one or more of the RNA subtractive hybridization probes in the hybridized complex specifically binds to an affinity label recognition molecule attached to the solid support, wherein the affinity label recognition molecule comprises streptavidin or neutravidin; and
    removing the 18S rRNA from the RNA sample by removing the complex comprising the hybridized complex and the solid support from the reaction composition;
    wherein a combination of polyethylene glycol and magnesium ions in the reaction composition enhances removal of the complex comprising the hybridized complex and the solid support from the reaction composition, and
    wherein the reaction composition consists of: polyethylene glycol at a concentration between about 2% and 25%, magnesium ions at a concentration between about 3 mM and 30 mM, and sodium chloride at a concentration about 150 mM.

2. The method of claim 1, further comprising recovering RNA remaining in the reaction composition after the removing step.

3. The method of claim 1, wherein one of the one or more RNA subtractive hybridization probes are derived from a 788 bp region of the 18S rRNA.

4. The method of claim 1, wherein the one or more of RNA subtractive hybridization probes are single-stranded RNA probes.

5. A method for removing 18S rRNA from an RNA sample, comprising:
    obtaining an RNA sample from a biological source;
    mixing said RNA sample with one or more RNA subtractive hybridization probes, thereby forming a mixture comprising the RNA sample and the one or more RNA subtractive hybridization probes, wherein the one or more RNA subtractive hybridization probes comprise an affinity label comprising biotin, and wherein the one or more the RNA subtractive hybridization probes hybridize to two or more discontinuous regions of 18S rRNA in the RNA sample;
    incubating the mixture under conditions effective to allow hybridization of the one or more RNA subtractive hybridization probes with the 18S rRNA in the RNA sample, thereby forming a hybridized complex comprising the one or more RNA subtractive hybridization probes and the 18S rRNA;
    facilitating association of the hybridized complex with a solid support by incubating the hybridized complex with the solid support in a reaction composition, thereby forming a complex comprising the hybridized complex and the solid support, wherein the affinity label on the one or more the RNA subtractive hybridization probes in the hybridized complex specifically binds to an affinity label recognition molecule attached to the solid support, wherein the affinity label recognition molecule comprises streptavidin or neutravidin; and
    removing the 18S rRNA from the RNA sample by removing the complex comprising the hybridized complex and the solid support from the reaction composition; and,
    wherein the reaction composition consists of: polyethylene glycol at a concentration between about 2% and 25%, magnesium ions at a concentration between about 3 mM and 30 mM, and sodium chloride at a concentration about 150 mM, and
    wherein a combination of the polyethylene glycol and the magnesium ions in the reaction composition enhances a removal of the complex comprising the hybridized complex and the solid support from the reaction composition.

6. The method of claim 5, wherein the RNA sample comprises a mixture of RNA from eukaryotic and prokaryotic cells.

7. The method of claim 5, wherein the one or more of RNA subtractive hybridization probes are single-stranded RNA probes.

* * * * *

SEQUENCE LISTING

<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: Synthetic sequence

<400> SEQUENCE: 1
taatacgact cactataggg                                            20

<210> SEQ ID NO 2
<211> LENGTH: 497

```
<212> TYPE: DNA
<213> ORGANISM: Artificial Sequence
<220> FEATURE:
<223> OTHER INFORMATION: Synthetic sequence

<400> SEQUENCE: 2
cgcgacctca gatcagacgt ggcgacccgc tgaatttaag catattagtc agcggaggag      60
aagaaactaa ccaggattcc ctcagtaacg gcgagtgaac agggaagagc ccagcgccga     120
atccttttgg acatgtggcg tacgaagac ccgctccttt ccaagtcct tctgatcgag       180 gcccagcccg tggacggtgt gaggccggta gcttttggtc ttcccggagt cgggttgctt    240
gggaatgcag cccaaagcgg gtggtaaact ccatctaagg ctaaataccg gcacgagacc    300
gatagtcaac aagtaccgta agggaaagtt gaaaagaact ttgaagagag agttcaagag    360
ggcgtgaaac cgttaagagg taaacgggtg gtttctcctcc cgaccctcc accctttac    420 cggctccggg acgctgggga aggttttcga cgtcggctac ccacccgacc cgtcttgaaa   480
cacggaccaa ggagtct                                                   497

<210> SEQ ID NO 3
<211> LENGTH: 499
<212> TYPE: DNA
<213> ORGANISM: Artificial Sequence
<220> FEATURE:
<223> OTHER INFORMATION: Synthetic sequence

<400> SEQUENCE: 3
aacacgtgcg cgagtcggtt ttggctcgca cgaaagccgc cgtggcgcaa tgaaggtgaa     60
ggttttcgag gtgggatccc gaggcctctc cagtcctttt ggaggtggag cacgagcgca   120
cgtgttagga cccgaaagat ggtgaactat gcctgggcag ggcgaagcca gaggaaactc   180
tggtggaggt ccgtagcggt cctgacgtgc aaatcggtcg tccgacctgg gtatagtttt   240
cgaaagacta atcgaaccat ctagtagctg gttccctccg aagtttccct caggatagct   300
ggcgctctcg cagacccgac gcaccttttc cacgcagttt tatccggtaa agcgaatgat   360
tagaggtctt ggttttcgaa acgatctcaa cctattctca aactttaaat gggtaagaag   420
cccggctcgc tggcgtggag cttttcgtgg aatgcgagtg cctagtgggc cacttttggt   480
aagcagaact ggcgctgcg                                                 499

<210> SEQ ID NO 4
<211> LENGTH: 493
<212> TYPE: DNA
<213> ORGANISM: Artificial Sequence
<220> FEATURE:
<223> OTHER INFORMATION: Synthetic sequence

<400> SEQUENCE: 4
ggatgaaccg aacgccgggt taaggcgccc gatgccgacg ctcatcagac cttttccaga     60
aaaggtgttg gttgatatag acagcaggac ggtggccatg gaagtcggaa tccgctaagg   120
agtgtgtaac aactcacctg ccgaatcaac tagccctgaa aatggatggc gctggagcgt   180
cgggcccata cccggccgtc gccggcagtc gagagtggac gggagctttt cgctgcggtg   240
agccttgaag cctagggttt tgcaggtgca gatcttggtg gtagtagcaa atattcaaac   300
gagaactttg aaggccgaag tggagaaggg ttccatgtga acagcagttg aacatgggtc   360
agtcggtcct gagagatggg cgagcgccgt tccgaaggga cgggcgatgg cctccgttgc   420
cctcggccga tcgaaaggga gtcgggttca gatccccgaa tccggagtgg cggagatggt   480
```

```
tttcgaggcg tcc                                                       493

<210> SEQ ID NO 5
<211> LENGTH: 498
<212> TYPE: DNA
<213> ORGANISM: Artificial Sequence
<220> FEATURE:
<223> OTHER INFORMATION: Synthetic sequence

<400> SEQUENCE: 5
agtgcggtaa cgcgaccgat cctttggag agttctcttt tctttgtgaa gggcaggttt     60
tcgtgccttg gaaagcgtcg cggttccggc ggcgtccggt gagctctcgc tggcccttga    120
aaatccgttt tggagagggt gtaaatctcg ttttcgtacc catatccgca gcaggtctcc    180
aaggtgaaca gcctctggca tgttggaaca atgtaggtaa gggaagtcgg caagccggat    240
ccgtaacttc gggataagga ttggctctaa gggctgggtc ggtcgttttc ctagcagccg    300
acttagaact ggtgcggacc aggggaatcc gactgtttaa ttaaaacaaa gcatcgcgaa    360
ggtttggtgt tgacgcgatg tgattctgc ccagtgctct gaatgtcaaa gtgaagaaat    420
tcaatgaagc gcgggtaaac ggcgggagta actatgactc tcttaaggta gccaaatgcc    480
tcgtcatcta attagtga                                                  498

<210> SEQ ID NO 6
<211> LENGTH: 498
<212> TYPE: DNA
<213> ORGANISM: Artificial Sequence
<220> FEATURE:
<223> OTHER INFORMATION: Synthetic sequence

<400> SEQUENCE: 6
cgcgcatgaa tggatgaacg agattcccac tgtccctacc tactatccag cgaaaccaca     60
gccaagggaa cgggcttggc ggaatcagct tttggaaaga agaccctgtt gagcttgact    120
ctagtctggc acggtgaaga gacatgagag gtgtagaata agtgggagtt ttggtgaaat    180
accactactc tgatcgtttt ttcactgacc ttttggtaca cctgtcaaac ggtaacgcag    240
gtgtcctaag gcgagctcag ggaggacaga aacctcccgt ggagcagaag ggcaaaagct    300
cgcttgatct tgattttcag tacgaataca gaccgtgaaa gcttttcctc acgatccttc    360
tgaccttttg ggttttaagc aggaggtgtc agaaaagtta ccacagggat aactggcttg    420
tggcggccaa gcgttcatag cgacgtcgct ttttgatcct tcgatgtcgg ctcttcctat    480
cattgtgaag cagaattc                                                  498

<210> SEQ ID NO 7
<211> LENGTH: 475
<212> TYPE: DNA
<213> ORGANISM: Artificial Sequence
<220> FEATURE:
<223> OTHER INFORMATION: Synthetic sequence

<400> SEQUENCE: 7
accaagcgtt ggattgttca cccactaata gggaacgtga gctgggttta gaccgtcgtg     60
agacaggtta gttttaccct actgatgatg tgttgttgcc atggtaatcc tgctcagtac    120
gagaggaacc gcaggttcag acatttggtg tatgtgcttg gctgaggagc caatggtttt    180
cgaagctacc atctgtggga ttatgactga acgcctctaa gtcagaatcc cgcccaggcg    240
gaacgatacg gcagcgccgc ggagcctcgg ttggcctcgg atagcttttg gtccggtgcg    300
```

-continued

```
gagtgccctt cgtcctggga aacgttttcg tcacgcaccg cacgttcgtg gttttgaacc    360
tggcgctaaa ccattcgtag acgacctgct tctgggtcgt tttggtttcg tacgtagcag    420
agcagctccc tcgctgcgat ctattgaaag tcagccctcg acacaagggt ttgtc         475
```